(12) United States Patent
Lin et al.

(10) Patent No.: US 10,342,549 B2
(45) Date of Patent: Jul. 9, 2019

(54) LUNG VOLUME-REDUCING ELASTIC IMPLANT AND INSTRUMENT

(71) Applicant: Lifetech Scientific (Shenzhen) Co., Ltd., Shenzhen (CN)

(72) Inventors: Weilin Lin, Shenzhen (CN); Siyi Li, Shenzhen (CN); Anning Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 273 days.

(21) Appl. No.: 15/317,222

(22) PCT Filed: May 29, 2015

(86) PCT No.: PCT/CN2015/080373
§ 371 (c)(1),
(2) Date: Dec. 8, 2016

(87) PCT Pub. No.: WO2015/188705
PCT Pub. Date: Dec. 17, 2015

(65) Prior Publication Data
US 2018/0132860 A1    May 17, 2018

(30) Foreign Application Priority Data
Jun. 11, 2014 (CN) .......................... 2014 1 0258067

(51) Int. Cl.
*A61F 2/04* (2013.01)
*A61B 17/12* (2006.01)
*A61B 17/00* (2006.01)

(52) U.S. Cl.
CPC .. *A61B 17/12145* (2013.01); *A61B 17/12104* (2013.01); *A61F 2/04* (2013.01);
(Continued)

(58) Field of Classification Search
CPC .......... A61B 17/12145; A61B 17/1215; A61B 17/12104; A61B 2017/00862;
(Continued)

(56) References Cited

U.S. PATENT DOCUMENTS

| | | | |
|---|---|---|---|
| 8,632,605 B2 * | 1/2014 | Thompson | A61B 17/12022 623/23.65 |
| 8,721,734 B2 * | 5/2014 | Mathis | A61B 1/2676 623/23.65 |
| 2005/0103340 A1 | 5/2005 | Wondka | |

FOREIGN PATENT DOCUMENTS

| | | |
|---|---|---|
| CN | 2749468 Y | 1/2006 |
| CN | 2749468 Y | 1/2006 |

(Continued)

OTHER PUBLICATIONS

International Search Report dated Aug. 26, 2015 for PCT/CN2015/080373.
(Continued)

*Primary Examiner* — Julian W Woo
(74) *Attorney, Agent, or Firm* — Raymond Sun

(57) ABSTRACT

A lung volume-reducing elastic implant (2) and a lung volume-reducing instrument; the lung volume-reducing elastic implant (2) is tubular and comprises a proximal implant end (201), an elastic deformation part (205) and a distal implant end (202); the elastic deformation part (205) is located between the proximal implant end (201) and the distal implant end (202), and the elastic deformation part (205) has a shape memory characteristic; the lung volume-reducing elastic implant (2) is opened at the proximal implant end (201); the elastic deformation part (205) is provided with a plurality of grooves (204) at intervals along the longitudinal direction thereof; each groove (204) communicates with the tube cavity of the elastic deformation part (205); the lung volume-reducing instrument comprises
(Continued)

the lung volume-reducing elastic implant (2) and a delivery device (1) matching same; the delivery device (1) comprises a guidewire (101) and a hollow push piece (110); the lung volume-reducing elastic implant (2) is detachably connected to the distal end of the hollow push piece (110) via the proximal implant end (201); and the guidewire (101) passes through the tube cavity of the lung volume-reducing elastic implant (2) and the tube cavity of the hollow push piece (110). The lung volume-reducing instrument is more convenient for an operation and takes shorter time, and avoids damage to the inner wall of the bronchia, reducing the occurrence of pneumothorax.

15 Claims, 8 Drawing Sheets

(52) U.S. Cl.
CPC . *A61B 17/1215* (2013.01); *A61B 2017/00309* (2013.01); *A61B 2017/00862* (2013.01); *A61B 2017/00867* (2013.01); *A61B 2017/1205* (2013.01); *A61F 2002/043* (2013.01)

(58) Field of Classification Search
CPC ... A61B 2017/00867; A61B 2017/1205; A61F 2/04; A61F 2002/043
See application file for complete search history.

(56) References Cited

FOREIGN PATENT DOCUMENTS

| | | | |
|---|---|---|---|
| CN | 2857885 | Y | 1/2007 |
| CN | 2857885 | Y | 1/2007 |
| CN | 102209570 | A | 10/2011 |
| CN | 202010169 | U | 10/2011 |
| CN | 202010169 | U | 10/2011 |
| CN | 102573700 | A | 7/2012 |
| CN | 102573700 | A | 7/2012 |
| WO | WO 03041779 | | 5/2003 |
| WO | WO03041779 | A1 | 5/2003 |
| WO | WO 2007138578 | | 12/2007 |
| WO | WO2007138578 | A2 | 12/2007 |

OTHER PUBLICATIONS

First office action in corresponding China application No. 201410258067.5.
PCT International Search Report for corresponding PCT application No. PCT/CN2015/080373.
PCT International Preliminary Report for corresponding PCT application No. PCT/CN2015/080373.
Search report in corresponding China application No. 201410258067.5.
First office action in corresponding Korean application No. 10-2017-7000646.

* cited by examiner

LUNG VOLUME-REDUCING ELASTIC IMPLANT AND INSTRUMENT

TECHNICAL FIELD

The present invention belongs to the technical field of interventional therapy, and relates to an implant and instrument for interventional therapy, in particular to a lung volume-reducing elastic implant and an instrument.

BACKGROUND ART

In clinical treatment, emphysema is a common pulmonary disease, particularly having a high incidence in the elderly. According to statistics, the survival rate of end-stage emphysema patients who have been sick for 5 years is less than 50 percent. Traditional emphysema medical treatment comprises oxygen inhalation, prevention of pulmonary infection, bronchia spasmolysis, etc. but curative effect is extremely limited. While the surgical treatment of emphysema is given priority to lung volume-reducing surgery, and there are also relatively large amounts of limitations, such as strict indications accompanied with relatively large amounts of complications, anesthesia and complications associated therewith, the curative effect is difficult to predict before surgery, any undesirable curative effect caused by too much or too little removal cannot be compensated after surgery, and the operative cost is high, and mental and physical pain is significant. Additionally, some patients with poor lung function often cannot tolerate the surgeries, therefore possessing high postoperative mortality, which limits the application of surgery.

In order to better treat emphysema, treatment for emphysema is carried out in the intervening modes with bronchoscope researched and utilized internationally, such as a unidirectional valve, xanthan gum, water vapor thermal ablation, and elastic coil for improving the quality of life for patients, and reducing the trauma to patients during surgery. Owing to the fact that the target area residual gas and sputum fails to be discharged effectively and actively, a unidirectional valve has poor clinical index, so the U.S. FDA has not approved this device. Additionally, the effectiveness of unidirectional valve treatment is further restricted by the technical difficulty of collateral ventilation and accurate positioning on different anatomical structures. The problem of postoperative inflammation has also not been adequately solved, due to the fact that the emphysema area is completely blocked by the xanthan gum. In addition, the water vapor is subjected to thermal ablation, which causes postoperative inflammation because of its damage to the original tissue structure of the emphysema area.

Currently, an updated treatment mode is adopted for the treatment of emphysema, that is to say, the elastic coil, as an implant, is implanted into the body pulmonary lesion site. FIG. 1 is a schematic diagram of a lung volume-reducing elastic coil of the prior art. The product is made up of nickel-titanium memory alloy metal wire for design, which can be subjected to elastic deformation under external force. The product, under the constraint of a delivery system, can be implanted into the lung with the bronchoscope working channel in the form of straight strips. After being delivered to the bronchia in the emphysema area, the coil is free from the constraints of the delivery system, recovering its shape to its natural shape (i.e. the shape being free from the external force) as shown in FIG. 1. Meanwhile, the emphysema area is extruded under the traction action of the nickel-titanium alloy wire, the gas in the bronchia is discharged, and the lung tissue volume in the emphysema area is reduced, such that the relatively healthy peripheral lung tissue gives play to better physiological function.

The surgical methods using the elastic coil comprise three operational processes of inserting the bronchoscope, establishing the channel, and implanting the coil. A schematic diagram showing the insertion of the bronchoscope 201 is shown in FIG. 2. A bronchoscope 201 is inserted through the mouth or nose, and an image detected by the distal end 203 of the bronchoscope is displayed on a monitor 204 via the bronchoscope 201, thereby guiding the bronchoscope 201 to reach the human pulmonary bronchia 205.

FIG. 2 also shows the establishment of the channel. The outer diameter of a guidewire 206 is about 5Fr to about 7Fr, while the tube diameter of a delivery sheath can be between about 5Fr and 9Fr. The guide wire 206 is inserted through the inner cavity of a dilator 207 which extends through the inner cavity of a delivery sheath 208, and the guidewire 206, the dilator 207 and the delivery sheath 208 are assembled together to enter the bronchoscope 201 through a working channel 202 of the bronchoscope 201 and to enter the bronchia 205 through the distal end 203 of the bronchoscope 201. A distal end 209 of the guidewire 206 is provided with a length marker 210, which indicates the distance along the guidewire 206 from the distal end 209. A distal end 211 of the delivery sheath 208 can be provided with a plurality of corresponding identifiers 210 in the form of high contrast metal strips (including gold, platinum, tantalum, iridium, tungsten and/or similar metal). The guidewire 206 can be guided using a fluoroscopy system with a remote imaging capture device 212, an ultrasonic imaging system, an MRI system, an X-ray computed tomography (CT) calculating system, or some other remote imaging implants. As shown in FIG. 2, the images detected can be displayed on a monitor 213 by the remote imaging capture device 212, and the track of the guidewire 206 or an imaging marker 210 can be identified by the remote imaging capture device 212, thereby establishing a channel.

After establishing the channel, the dilator 207 and the guidewire 206 are withdrawn from the delivery sheath 208 towards the proximal end, thereby delivering a lung volume-reducing elastic coil 301 in an open cavity of the delivery sheath 208. FIG. 3 is a schematic diagram showing the implanting of the coil 301. A delivery system 302 loaded with the coil 301 is coupled to the proximal end of the delivery sheath 208 by a locking hub connection 303. As shown in FIG. 4, the coil 301 is introduced to the delivering sheath tube, and the coil 301 is pushed out of the distal end of the delivering sheath tube 208 by a wireline 305 of an actuating device 304, thereby entering the bronchia 205. The delivering sheath tube 208 is then withdrawn, and the coil 301 is released by a gripper 306 of the actuating device 304. The coil 301 further pulls the bronchia 205 to curl while the coil 301 recovers into its original shape, thereby achieving the curative effect of reducing the volume of emphysema.

The above implants and the implanting methods thereof have the following shortcomings:

1. The elastic coil made from the prior nickel-titanium wire needs to be released by the delivery sheath, and the inner wall of the bronchia might be injured when the delivery sheath is pushed in the bronchia, causing adverse effects such as pneumothorax.

2. Owing to relatively large outer diameter of the delivery sheath of about 5Fr to 9Fr, it is difficult to implant the elastic coil into the tail end of the lung bypass or each of some small-diameter tracheae via the delivery sheath, and the range of emphysema area pressed and pushed by the elastic coil is limited, thereby affecting the volume-reduction effect.

3. The present surgical method of inserting the elastic coil requires three independently operated processes of inserting the bronchoscope, establishing the channel, and implanting the coils, which takes a long time to complete the procedure. In addition, the procedure is performed when the patient is sober, easily causing adverse events such as COPD acute exacerbation and the like due to the extended procedure time.

SUMMARY OF THE INVENTION

The technical problem to be solved by the present invention is to provide an implant directly delivered by using a guidewire instead of a delivery sheath in order to overcome the aforesaid shortcomings in the prior art. By using the implant, injury to the inner wall of the bronchia by the delivery sheath can be avoided, and the occurrence rate of pneumothorax is reduced.

The technical problem to be further solved by the present invention is to provide a lung volume-reducing instrument capable of being implanted at the tail end of a lung bypass or each of some small-diameter tracheae according to actual requirements, where the channel establishing process and the implant implanting operation process can be combined, so that the operation process is more convenient, the operation time is reduced, and a better treatment effect is achieved.

A lung volume-reducing elastic implant which is tubular and comprises a proximal end, an elastic deformation part and a distalt end, the elastic deformation part is located between the proximal end and the distal end and at least the elastic deformation has a shape memory characteristic, at least the proximal end of the lung volume-reducing elastic implant is opened, the elastic deformation part is provided with a plurality of grooves at intervals along the longitudinal direction thereof, and each groove communicates with a tube cavity of the elastic deformation part.

In one embodiment of the technical scheme, included angles α formed by the cut directions of the grooves and the length direction of the elastic deformation part are 10-90° on the axially split spreading plane of the lung volume-reducing elastic implant; and the shapes and arrangement of the grooves satisfy multidirectional bending and twisting of the elastic deformation part and meet the bending stress requirement of the implant.

In one embodiment of the technical scheme, the implant also comprises an elastic membrane coating the outer wall of the elastic deformation part.

In one embodiment of the technical scheme, the elastic membrane can also coat the surface of the whole implant and fills the grooves.

In one embodiment of the technical scheme, the outer diameter of the implant is gradually increased from the distal end to the proximal end.

In one embodiment of the technical scheme, the proximal end of the implant and the proximal end of the elastic deformation part form an integrated structure.

In one embodiment of the technical scheme, the distal end of the implant extends outward to be connected with a flexible implant guide head, the implant guide head is coaxial with the distal end of the implant and closes the distal end of the implant, and the implant guide head is provided with a developing identifier.

In one embodiment of the technical scheme, the proximal end of the implant is provided with a detachable connecting piece in the lung volume-reducing elastic implant.

A technical scheme adopted by the present invention also provides a lung volume-reducing instrument comprising any one of the above implants, and a conveying, device matched with the implant, wherein the conveying device comprises a guidewire and a hollow push piece, the implant is detachably connected to the distal end of the hollow push piece via the proximal implant end, and the guidewire movably passes through the tube cavity of the implant and the tube cavity of the hollow push piece.

In one embodiment of the technical scheme, the distal end of the guidewire is provided with a flexible guidewire guide head coaxial with the guidewire, and the guidewire guide head has an outer diameter consistent with that of the guidewire.

In one embodiment of the technical scheme, the flexible guidewire guide head can be provided with a developing identifier.

In one embodiment of the technical scheme, the flexible guidewire guide head comprises a guide post, and a spring fixed and sleeved outside the guide post, and the guide post and the guidewire are integrally structured or the guide post is fixedly connected to the distal end of the guidewire, and the spring has a developing identifier.

Compared with the prior art, the implant provided by the present invention is tubular and is opened at least at the proximal end to ensure that the guidewire can be directly penetrated into the tube cavity of the implant to restrain the implant to form straight strips to be delivered, so that the implant does not need to be restrained by the delivery sheath with the outer diameter larger than that of the implant, so that the injury of the delivery sheath to the tracheae in the delivery process is avoided, and the occurrence rate of pneumothorax is further reduced. On the other hand, the implant can be opened at both the proximal end and the distal end or only opened at the proximal end. When the implant is opened at both the proximal end and the distal end, the guidewire can be utilized to directly guide in the trachea and establish the channel. When the implant is only opened at the proximal end, the implant can comprise the flexible guide head arranged at the distal end of the implant and used for closing the distal end of the implant, at this moment, the flexible guide head can be utilized to directly guide in the trachea and establish the channel by way of inserting the guidewire into the tube cavity of the implant and restraining the flexible guide head. Through loading and releasing by using the guidewire, the implant can be implanted to the tail end of the lung bypass or each of some small-diameter tracheae to extrude an emphysema area so that the lung interventional curative effect is achieved.

The implant of the present invention has a hollow tubular cavity structure, which facilitates the pre-threading of the guidewire through a tubular cavity of the implant during operation, so that the implant is loaded onto the guidewire, the implant and the guidewire are collectively pushed into the bronchia of an emphysema area by virtue of a bronchoscope, as described above, and the guidewire or the implant is used to establish a channel. After the implant is pushed to an appropriate target area, the guidewire is withdrawn to release the implant, so that two operation processes (i.e. a channel establishing process and an implantation process) of the implant in the prior art are synchronously completed, and the operation time can be effectively reduced, thereby avoiding adverse events such as COPD acute exacerbation and the like.

Moreover, the elastic deformation part of the implant or the whole implant is coated with an elastic membrane, so that a metal surface of the implant can be prevented from directly contacting an inner wall of the bronchia, and the release of metal elements is reduced, thereby effectively reducing pneumonia or small airway infection.

An instrument of the present invention utilizes the guidewire to load the implant, as well as guides and establishes the channel, to deliver the implant and to release the implant; or the implant distal end is provided with a soft implant guide head, the implant guide head may play a role in guiding and establishing the channel, and the implant can be immediately released after the channel is established; and the channel establishing process and the implantation operation process of the implant are combined by utilizing the solution, so that the operation is more convenient, and the operation time can also be reduced.

In the instrument of the present invention, a conveying device uses the guidewire to pass through the implant with the tubular cavity structure, the implant is delivered by virtue of the pushing of a push mechanism, by means of the constraint of the guidewire, the implant is transitioned from a natural state (i.e. a predetermined curly state obtained after the heat treatment) to a delivery state (i.e. a straight strip shape matched with the shape of the guidewire). After the guidewire is withdrawn from the tubular cavity of the implant, the constraint of the guidewire is released, and the implant can be transitioned from the delivery state to the natural state, thereby achieving an effect of extruding an emphysema target area. Compared with the prior art which uses a delivery sheath, the diameter of the conveying device is smaller, so that the implant can enter a smaller emphysema target area, and a better curative effect can be achieved. By adopting a technical solution combining the establishment of the channel and the release of the implant, the present invention can shorten the whole operation time, and can be more precisely positioned in the emphysema target area.

The instrument of the present invention also adopts the elastic membrane to coat the surface of the implant, and the elastic membrane is made from a high molecular material with better biological compatibility, so that the elastic membrane of the high molecular material contacts the inner wall of the bronchia, compared with the solution adopting a nickel-titanium wire to directly contact the inner wall of the bronchia in the prior art. Thus, the inflammation and injury of the bronchia caused by the friction between the implant and the inner wall of the bronchia in the breathing process can be reduced, thereby reducing the risk of pneumonia and small airway infection. Additionally, the metal surface of the implant is coated with the elastic membrane of the high molecular material, thereby effectively reducing the release of the metal elements.

BRIEF DESCRIPTION OF THE DRAWINGS

The present invention is further described below with reference to the drawings and embodiments, and in the drawings.

DETAILED DESCRIPTION OF THE INVENTION

In order to more clearly understand technical features, objectives and effects of the present invention, the embodiments of the present invention are described in detail with reference to the drawings.

Figure 1:
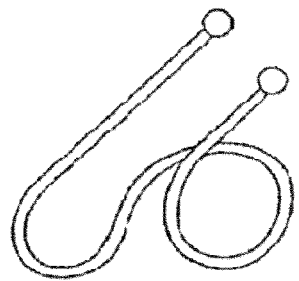
FIG. 1 is a structural schematic diagram of an elastic coil in the prior art.
Figure 2:
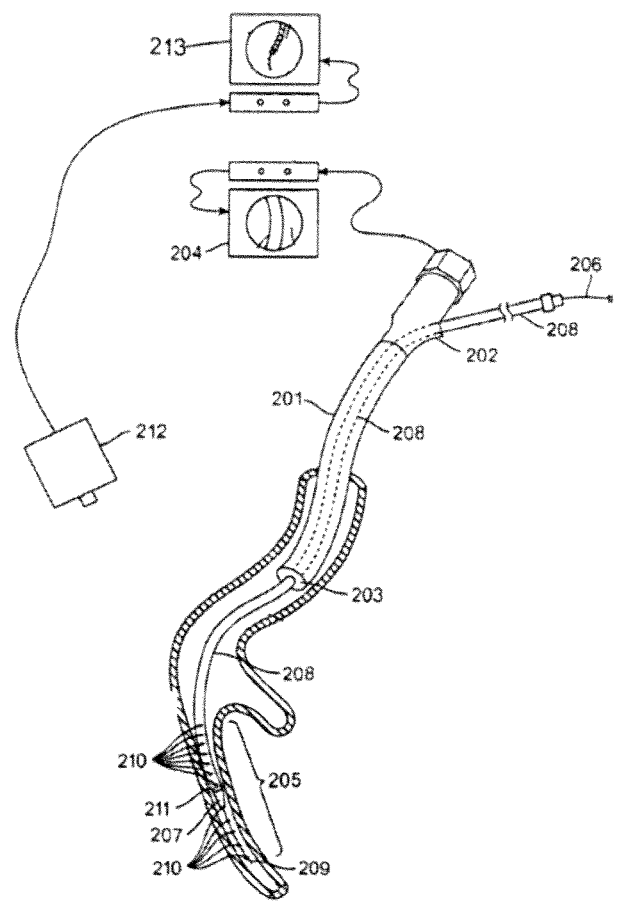
FIG. 2 is a schematic diagram showing the implantation of a bronchoscope and the establishment of a channel by a guidewire in the prior art.
Figure 3:
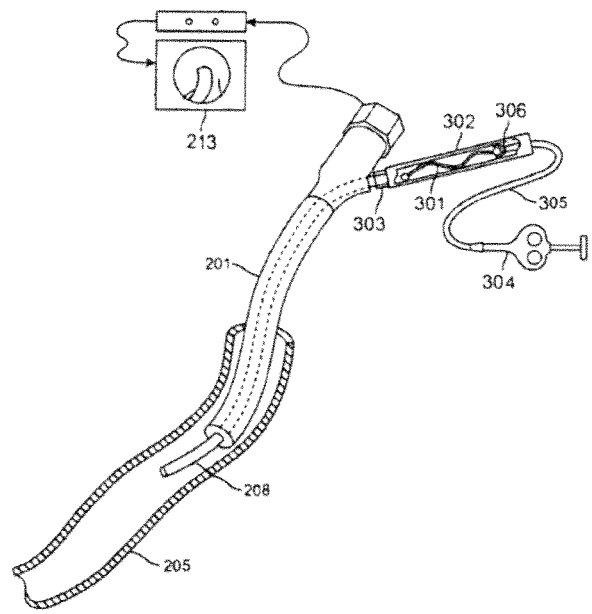
FIG. 3 is a schematic diagram showing the delivery of an elastic coil in the prior art.
Figure 4:
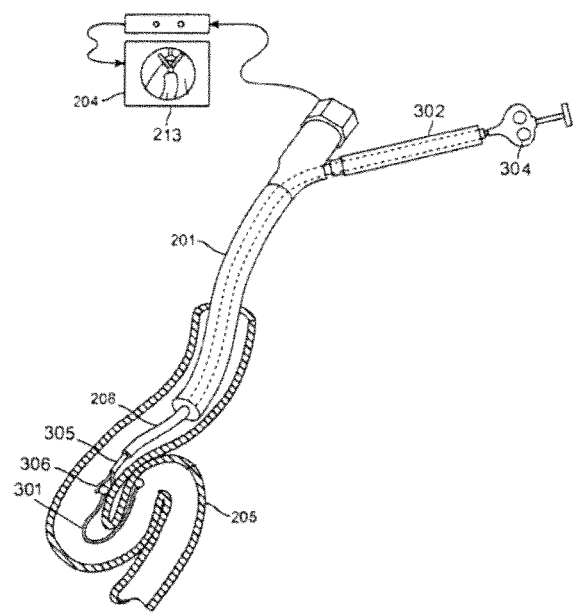
FIG. 4 is a schematic diagram showing the release of an elastic coil in the prior art.
Figure 5:
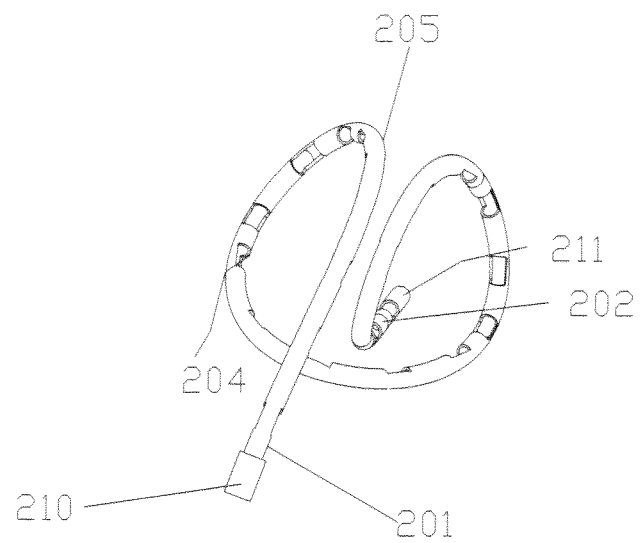
FIG. 5 is a structural schematic diagram of an implant provided by an embodiment of the present invention.
Figure 6:
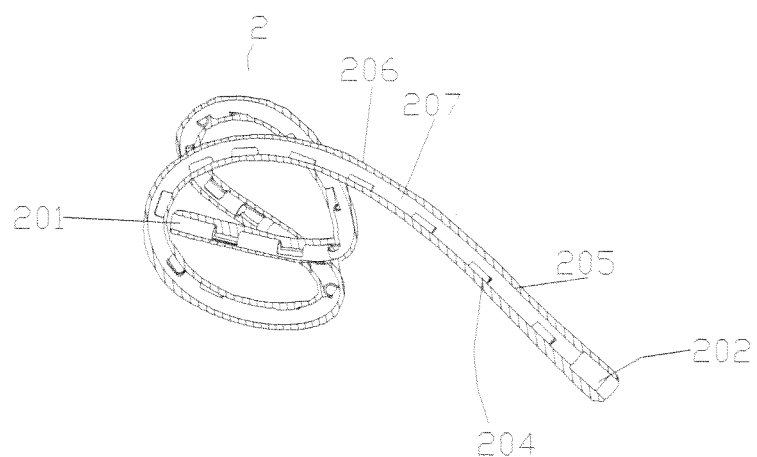
FIG. 6 is a sectional view of the implant as shown in FIG. 5.

As shown in FIG. 5 and FIG. 6, an embodiment of the present invention provides a lung volume-reducing elastic implant, wherein the implant 2 is in a tubular shape and comprises an implant proximal end 201, an elastic deformation part 205 and an implant distal end 202. The elastic deformation part 205 is disposed between the implant proximal end 201 and the implant distal end 202, and the elastic deformation part 205 at least has a shape memory characteristic. The implant proximal end 201 in the implant 2 is opened (the proximal end refers to the end closest to a surgical operator), and the three main parts of the implant 2 can be an integrated structure in one piece, and can also be separate pieces fixedly connected with one another.

The elastic deformation part 205 comprises a tube cavity or lumen 207. The elastic deformation part 205 is provided with a plurality of grooves 204 in the axial direction. i.e. the longitudinal direction, and the grooves 204 communicate with the tube cavity 207. The elastic deformation part 205 is the main structure of the implant 2, is in a predetermined curved shape in its natural state (i.e. not subjected to any external force), can be constrained to form straight strips or any other shapes under the effect of an external force, and can recover its predetermined shape through bending and twisting after the external force is removed. The implant 2 can be made from a material often used in the industry and having a shape memory characteristic; specific materials are not limited in the present invention, and any material suitable for use in the human body and having a shape memory characteristic can be used. In the embodiment, the implant 2 is made from nickel-titanium alloy, specifically a hollow nickel-titanium tube. Particularly, after certain grooves 204 are cut in a raw material for the hollow nickel-titanium tube, the nickel-titanium tube is bent to be in a predetermined shape and then is subjected to heating treatment and shaping to obtain the implant 2.

The outer diameter and inner diameter of the implant 2 depend on its characteristics and the outer diameter of the guide wire. That is based on the premise that sufficient elastic force is maintained for traction of the lung tissues, the implant 2 is implanted into the tail end of the lung bypass or each of some small-diameter tracheae to achieve a better curative effect. In addition, the inner diameter of the implant 2 should be greater than the outer diameter of the guide wire. In one embodiment, the outer diameter of the implant 2 is 0.5 to 2.5 mm, and the wall thickness can be 0.01 to 0.5 mm.

The implant 2 can be an equal-diameter tube with the outer diameter and the inner diameter maintained constant from one end to the other end, and can also be a non-equal-diameter tube having a variation in the outer diameter and the inner diameter. The implant 2 can extend into the thinner bronchia, in other embodiments of the present invention, the implant 2 can be a tapered tube of which the tube cavity 207 does not vary in diameter but the tube wall is gradually increased in thickness from the distal end to the proximal end. In other words, the outer diameter of the implant 2 is gradually increased from the distal end to the proximal end. For example, the tapered tube with an inner diameter of 0.8 to 10 mm is selected, and the wall thickness of the tapered tube changes from 0.01 mm at the distal implant end 202 to 0.2 mm at the proximal implant end 201.

Larger-curvature bending of the elastic deformation part 205 can be achieved through the existing grooves 204. Twisting at various different angles of the elastic deformation part 205 can be achieved, and accordingly complex predetermined shapes can be formed. In the present invention, the arrangement of the grooves 204 is not limited, the grooves 204 are generally arranged in a variety of modes, such as parallel mode and spiral mode, viewed from the peripheral direction of elastic deformation part 205. The grooves 204 can also be arranged locally and can also be wholly arranged in the peripheral direction of the elastic deformation part 205. The grooves 204 can be of a variety of structures, for example, the grooves 204 can be generally of long and narrow structures. Axial included angles α formed by the grooves 204 and the elastic deformation part 205 are 10 to 90° on the axially split spreading plane of the elastic deformation part 205; i.e. the included angles α formed by the opening directions of the grooves 204 and the elastic deformation part 205 are 10 to 90°. The arrangement of the grooves 204 aims at better bending and twisting, unparalleled axes of the grooves 204, and the elastic deformation part 205 facilitates bending of the elastic deformation part 205. As a result, with the included angles α being 10 to 90°, the bending of the elastic deformation part 205 within the same plane is facilitated, and bending and twisting can be simultaneously achieved at included angles α which are smaller than 90° so that the elastic deformation part 205 can be formed within the range of 360 degrees. In other embodiments of the present invention, the axial included angles α formed by the grooves 204 and the elastic deformation part 205 are preferably 45 to 90°. The shapes, quantity, arrangement density and positions of the grooves 204 should satisfy multidirectional bending and twisting of the elastic deformation part 205, the arrangement positions, quantity, shapes and arrangement density of the grooves 204 should also meet the requirement for exerting a bending stress extruding the lung tissue after the implant 2 is implanted into the lung tissue. In other words, the implant 2 is prevented from puncturing the bronchia when pulling the tissues in the emphysema area in the shape recovering process. The grooves 204 can be specifically formed according to actual calculation, so that when the implant 2 is implanted into the lung, bronchial puncture caused by excessive local stress is not created, and the injury caused by the implant 2 to the human body due to injury or breakage caused by the excessive stress is also avoided.

Figure 7:
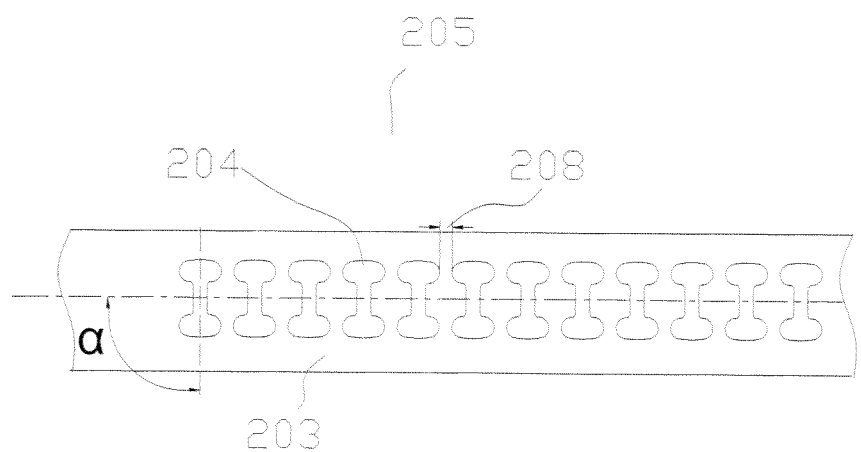
FIG. 7 is a schematic diagram of a groove after the implant provided in one embodiment of the present invention is dissected and unfolded along a longitudinal direction.
Figure 8:
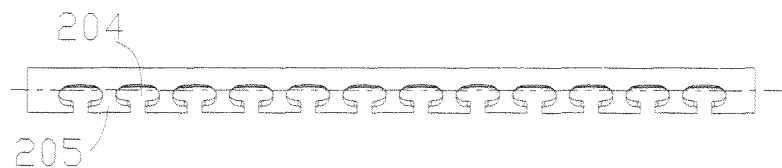
FIG. 8 is a schematic diagram of a groove after an elastic deformation part of the implant provided in another embodiment of the present invention is constrained into a straight strip.

In the embodiment shown in FIGS. 7 and 8, the single groove 204 is dumbbell-shaped, and it can be seen from the axially split spreading plane view of the elastic deformation part 205 shown in FIG. 7 that the axial included angles α formed by the grooves 204 and the elastic deformation part 205 are 90°. Multiple grooves 204 are continuously formed at equal intervals, and all the grooves 204 are parallel to each other. The dumbbell-shaped grooves 204 can satisfy the bending and twisting of the elastic deformation part 205. Intervals 208 of about 0.05 to 0.5 mm exist between the grooves 204. The outer diameter of the elastic deformation part 205 is 0.5 to 1.5 mm, and the wall thickness is 0.01-0.2 mm.

Figure 10:
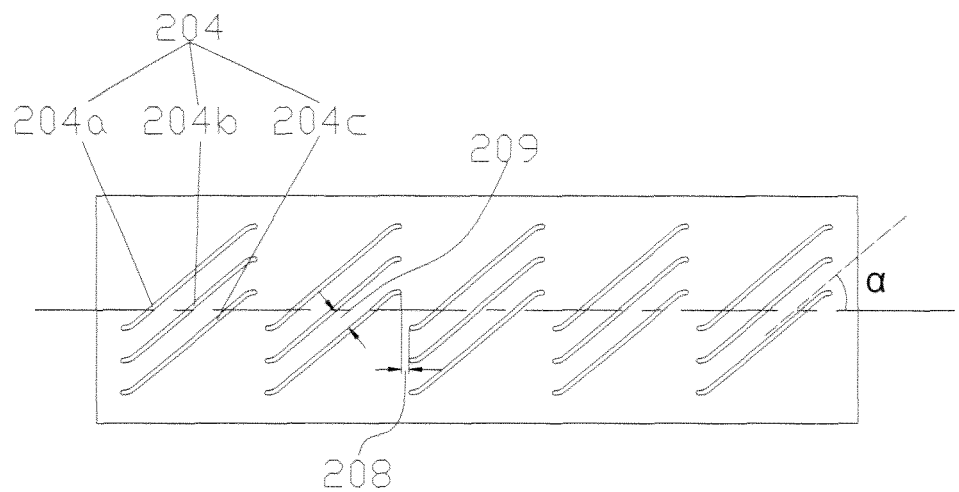
FIG. 10 is an expanded view of an implementation method of a groove of an implant provided in another embodiment of the present invention.
Figure 11:
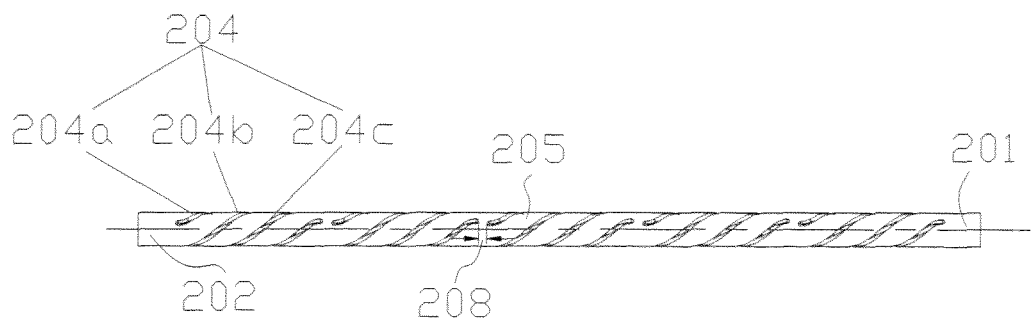
FIG. 11 is a local schematic diagram of an elastic deformation part of the implant shown in FIG. 10.

In another embodiment of the present invention shown in FIGS. 10 and 11, the elastic deformation part 205 is provided with multiple groups of grooves 204. After the elastic deformation part is split axially and spread flat, it can be seen that each group of grooves 204 includes three grooves 204a, 204b and 204c arranged in the peripheral direction of the elastic deformation part 205, and two ends of each of the three grooves are mutually aligned in the peripheral direction. The grooves 204a, 204b and 204c have a certain interval 209, and an interval 208 is provided between every two adjacent groups of grooves 204. The grooves 204 of the long and thin structures, the extending directions of these grooves 204 and the axis of the elastic deformation part 205 form certain included angles α. The bending stress of the whole elastic deformation part 205 can be adjusted by adjusting the number and the intervals 209 of all groups of parallel grooves 204, the included angles α formed by the grooves 204, and the axis of the elastic deformation part 205 and the intervals 208 among all groups of parallel grooves 204, to allow the elastic deformation part 205 to meet the clinical requirements. In other embodiments, the number of grooves in each group of grooves 204 can be 2 to 6, the interval 209 between every two adjacent grooves 204 can be 0.05 to 1 mm, the included angles α can be 10 to 85°, and the interval 208 between every two adjacent groups is 0.1 to 1.0 mm. The outer diameter of the elastic deformation part 205 is 10 to 2.0 mm, and the wall thickness is 0.05 to 0.3 mm.

Figure 12:
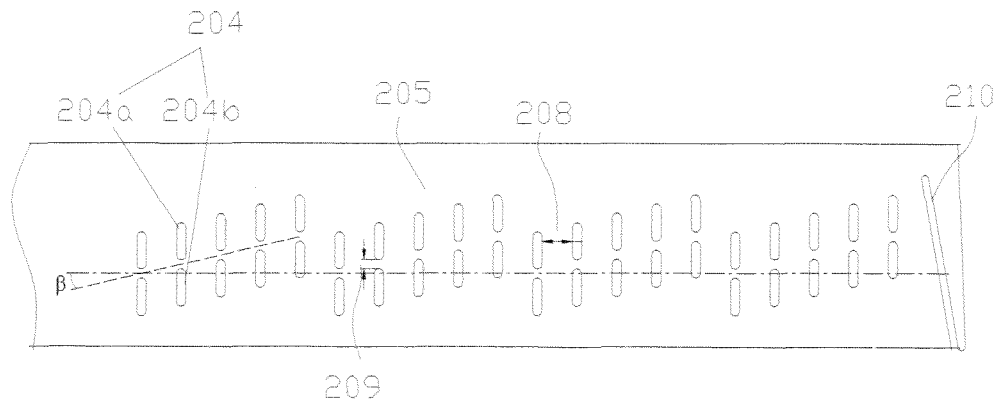
FIG. 12 is an expanded view of another implementation method of a groove of an implant provided in a further embodiment of the present invention.
Figure 13:
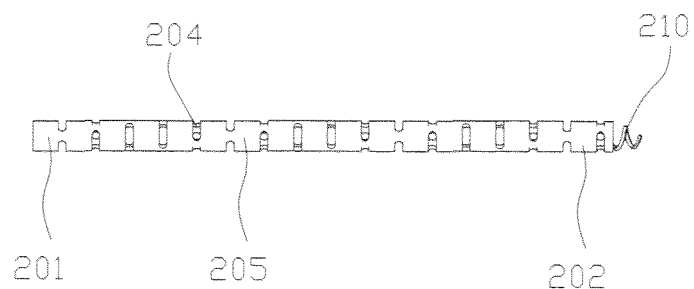
FIG. 13 is a local schematic diagram of an elastic deformation part of the implant shown in FIG. 12.

In another embodiment of the present invention shown in FIGS. 12 and 13, the middle section of the elastic deformation part 205 is divided into multiple groups of prolated elliptoid grooves 204, and each group of grooves 204 consists of more than two side-by-side elliptoid grooves 204. In the embodiment, each group of grooves 204 consists of the grooves 204a and 204b which are arranged in an iterated mode, a certain interval 209 is provided between the grooves 204a and 204b, the included angles α formed by the grooves 204 and the axis of the elastic deformation part 205 are 90°, and the extending direction in which the groups are arranged and the axis of the elastic deformation part 205 form a certain included angle β. The included angle β can be 60 to 90°, intervals 208 of 0.3 to 5 mm are provided among the groups of grooves 204, and the groups of grooves 204 are periodically arranged in a stepped mode. For example, 5 to 20 groups of grooves 204 can form a period, and the grooves 204 periodically arranged in the stepped mode facilitates formation of the specific shape of the elastic deformation part 205 through bending. The proximal implant end 201 and the distal implant end 202, which are about 1.5 to 10 mm long, are arranged at two ends of the elastic deformation part 205, and a section of about 0.5 to 5 mm long of the proximal implant end 201 is cut into a threaded groove to serve as a connecting piece 210. The cut implant 2 is then bent to be in the shape shown in FIG. 14 by using a mold, and the implant 2 is formed through heat treatment and shaping. In the embodiment, the outer diameter of the implant 2 is 12 to 2.5 mm, and the wall thickness is 0.1 to 0.4 mm.

Figure 14:
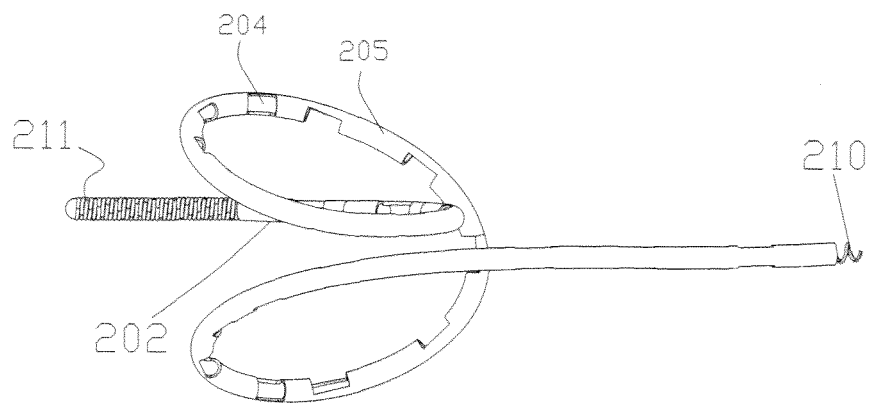
FIG. 14 is a structural schematic diagram of an implant with a connecting piece and a skeleton guide head provided in an embodiment of the present invention.

As shown in FIGS. 5 and 14, the proximal implant end 201 and the distal implant end 202 are respectively arranged at two ends of the elastic deformation part 205, wherein the proximal implant end 201 is used for arranging the connecting piece 210, and the distal implant end 202 is used for entering the bronchia in advance. The proximal implant end 201 is connected with the connecting piece 210 for use in detachably connecting with a push mechanism (such as the hollow push steel cable). In the present invention, the detachable connection mode refers to the connecting piece 210 being fixed to the push mechanism together before pushing and during pushing, and the connecting piece 210 breaks away from the push mechanism after the implant 2 is positioned at the desired location. There are a variety of structures detachably connected with the connecting piece 210 and a variety of connection modes. As shown in FIG. 5, the threaded connection is adopted, and the connecting piece 210 with inner thread is welded at the proximal implant end 201. During assembly, the connecting piece 210 can be in threaded connection with a push mechanism having an outer thread; after a corresponding position is reached through pushing, the connecting piece 210 can be separated from the push mechanism by twisting the push mechanism. Obviously, based on the prior art, the connecting piece 210 can be made of other detachable parts, such as a magnetic connecting device, an elastic fastener, and a lasso, which are respectively arranged at the proximal implant end 201 of the implant 2 and the push mechanism to achieve the detachable connection. Alternatively inner threads can be directly lathed on to the proximal implant end 201 to serve as the connecting piece 210 (namely, the proximal implant end 201 can be a part of the elastic deformation part 205). As shown in FIG. 14, the connecting piece 210 arranged at the proximal implant end 201 is of a spiral connecting hook, similarly, a spiral connecting hook is also arranged on the push mechanism, and they are mutually and rotatable hooked together so that the implant 2 can be detachably and fixedly connected at the distal end of the push mechanism.

As shown in FIG. 14, for enabling the implant 2 to smoothly enter the trachea, the distal implant end 202 is extended outwardly to be connected with a flexible implant guide head 211 when the distal end of the implant 2 is not opened, wherein the implant guide head 211 is coaxial with the distal implant end 202 and closes the distal implant end 202, and the implant guide head 211 is provided with a developing identifier. The implant guide head 211 provides guidance and establishes a channel, and can form an integral structure with the distal implant end 202 and can also be additionally fixed to the distal implant end 202. The implant guide head 211 has relative flexibility to avoid scratching the tracheal wall after entering the trachea. The developing identifier is configured to facilitate monitoring in the pushing process and can allow the implant 2 to be displayed through a fluoroscopy system, an ultrasonic imaging system, an MRI system, a computed X-ray tomography (CT) system or other remote imaging systems, among others. The implant 2 is displayed and guided through these systems, and in the embodiment, a spring, which is 1 to 10 mm long and is formed by winding tungsten, tantalum and other metal wires with the diameters of 0.1 to 0.5 mm and having strong X-ray developing characteristic, serves as the developing identifier. In the embodiment, the developing identifier and the implant guide head 211 are integrated into one part to achieve two functions. Except the mode, a developing identifier can also be additionally arranged on the implant guide head 211, for example a developing ring can be used where the implant guide head 211 is sleeved with the developing ring.

Figure 9:
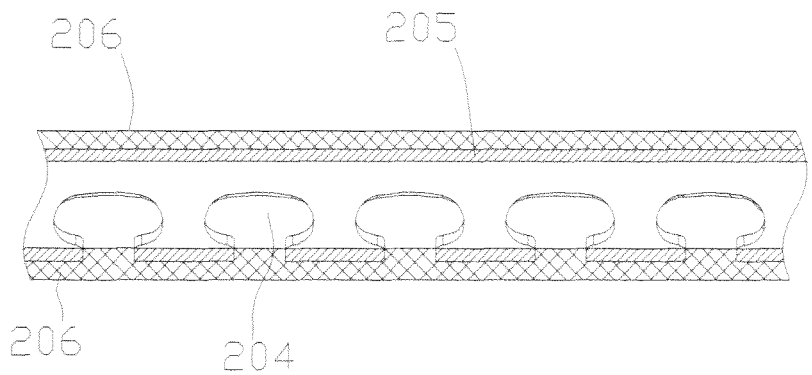
FIG. 9 is a local sectional view of the implant as shown in FIG. 8.

As shown in FIGS. 6 and 9, in the above embodiments, the elastic deformation part 205 can further be externally coated with an elastic membrane 206. In one embodiment, the elastic membrane 206 coats each of the elastic deformation part 205, the proximal implant end 201 and the distal implant end 202, so that the bronchia is not damaged in the implanting process of the whole implant 2. The grooves 204 can be filled with the elastic membrane 206 to ensure that the overall surface of the implant 2 is smooth, and the grooves 204 are filled with the elastic membrane 206 so that the elastic membrane 206 can firmly coat the surface of the implant 2. Meanwhile, for ensuring smoothness in the tube cavity 207 of the elastic deformation part 205, the inner wall formed by the elastic membrane 206 in the grooves 204 is aligned with the inner wall of the tube cavity 207 of the elastic deformation part 205. The thickness of the elastic membrane 206 can be 0.01 to 0.3 mm. The elastic membrane 206 can be made from high-molecular materials having excellent chemical stability, water-proofing, and weather-aging resistance, good low compressibility, good biocompatibility, high mechanical strength, non-toxicity, and can be odorless, among other characteristics. For example, these high-molecular materials can be silicone rubber or polyurethane materials. When the implant guide head 211 is provided, the elastic membrane 206 coats the elastic deformation part 205 and the implant guide head 211 thereof simultaneously to form the elastic membrane 206 with an integrated structure.

Figure 15:
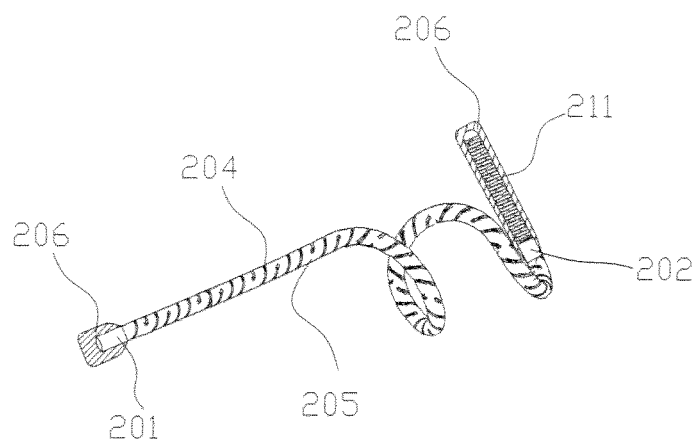
FIG. 15 is a structural schematic diagram of an implant reserving a local elastic membrane provided in an embodiment of the present invention.

FIG. 15 is a sectional view of the implant 2 with the local elastic membrane 206 provided by one embodiment of the present invention, and the deformation part of the elastic deformation part 205 including multiple groups of grooves 204. The surfaces of the elastic deformation part 205, the proximal implant end 201, the distal implant end 202 and the implant guide head 211 are coated with a layer of elastic membrane 206.

It is worth mentioning that the two ends of the lung volume-reducing, elastic implant 2 of one embodiment of the invention are opened, namely both the proximal implant end 201 and the distal implant end 202 are open, and it is possible for the implant 2 to not include the implant guide head 211.

One embodiment of the invention further provides a lung volume-reducing, instrument, as shown in FIGS. 1 to 21, which comprises the implant 2 and a delivery device 1, wherein the implant 2 is of a tubular structure having a shape memory characteristic, the body of the implant 2 is the elastic deformation part 205, and the elastic deformation part 205 is provided with a tube cavity 207. The two ends of the implant 2 are the proximal implant end 201 and the distal implant end 202, a plurality of grooves 204 are formed in the surface of the elastic deformation part 205 and extend through the tube cavity 207 of the elastic deformation part 205. The deliver device 1 comprises a guide wire 101 and a push mechanism 110 (generally, the push mechanism 110 comprises a hollow push piece, namely a hollow steel cable 103, and a control handle 106 connected with the hollow steel cable 103). The implant 2 is detachably connected to the distal end of the push mechanism 110 through the connecting piece 210, the guide wire 101 extends through a lumen of the implant and the hollow steel cable 103 respectively. In other words, the guide wire 101 is loaded in the implant 2 and the hollow steel cable 103, and the implant 2 can move along the guide wire 101.

In the delivery device 1, the guide wire 101 is used for holding and guiding implant 2, and establishing a channel. The implant 2 encloses the guide wire 101, and the implant 2 is constrained to be in a straight strip shape by the guide wire 101. In other words, the implant 2 is stretched by the guide wire 101 to be in a straight delivery state that is aligned with the shape of the guide wire 101 to facilitate access to the bronchia.

Figure 16:
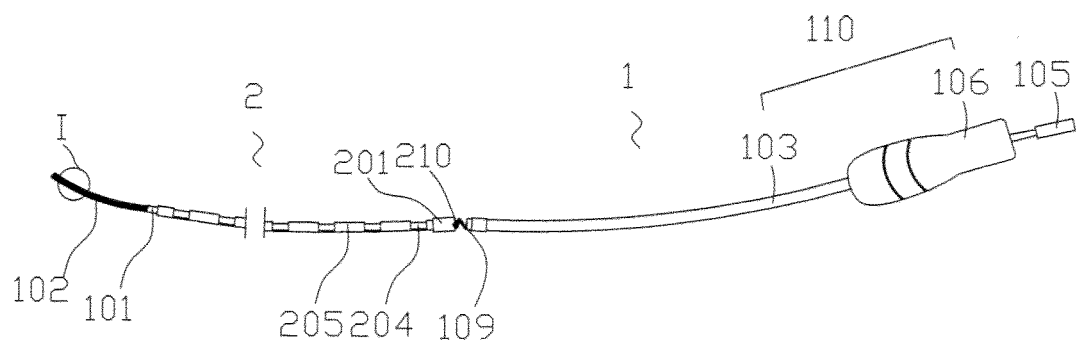
FIG. 16 is a schematic diagram of a lung volume-reducing instrument provided in an embodiment of the present invention.

Referring to FIG. 16, the guide wire 101 can be inserted into the proximal implant end 201 of the implant 2, and the guide wire 101 can be made of a metal wire with the diameter of 0.1 to 1.1 mm. The guide wire 101 has the roles of establishing the channel and delivering the implant 2 to a diseased part, accordingly a sheath is no longer needed for constraining the implant 2, so that injury caused by a sheath to the bronchia is also avoided, and the occurrence rate of pneumothorax is further reduced. The metal wire has a certain rigidity and toughness, can be properly bent, fits with the shape of the bronchia, and can advance step by step along the trachea. Compared with the prior art, due to the fact that a sheath is no longer needed in the delivery process, the implant 2 can be implanted into the tail end of the lung bypass or each of some small-diameter tracheae to achieve a good curative effect.

Figure 17:
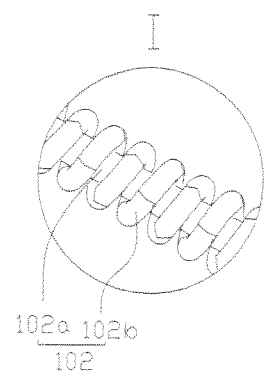
FIG. 17 is an enlarged view of the position 1 in FIG. 16.

For achieving safe and convenient operation, a soft guide wire guide head 102 coaxial with the guide wire 101 and provided with a developing identifier is arranged at the distal end of the guide wire 101, with the guide wire guide head 102 consistent with the guide wire 101 in outer diameter. As shown in FIG. 17, the guide wire guide head 102 comprises a guide post 102a and a spring 102b fixed and sheathed outside of the guide post 102a, and the guide post 102a forms an integral structure with the guide wire 101 or is fixedly connected to the distal end of the guide wire 101. The spring 102b can have a developing identifier.

The guide wire guide head 102 can effectively avoid injury to the tracheal wall during implantation into the trachea because of the softening of the distal end of the guide wire 101. The soft guide wire guide head 102 can be achieved through the spring that has a soft characteristic; i.e. the guide post 102a forming the integral structure with the guide wire 101 or fixedly connected to the distal end of the guide wire 101 is sheathed with the spring 102b. The specific manufacturing process is that the head end of the guide wire 101 is thinned and then is manufactured into the guide post 102a, and then the spring 102b with the length of 5 to 150 mm is fixed to the outside of the guide post 102a. The fixing mode of the spring 102b and the guide wire 101 can be macromolecular heat shrinkable tube or film coating, adhesive bonding, laser welding, tin soldering and on the like. Under the guidance of the soft guide wire guide head 102, the guide wire 101 can smoothly enter the tube cavity 207 of the elastic deformation part 205 from the proximal implant end 201 of the implant 2, and the implant 2 can be constrained from the shape shown in FIGS. 5 and 6 into the straight delivery state, as shown in FIG. 16. Based on the prior art, the guide wire 101 loaded with the implant 2 also controls guidance and establishes the channel in the bronchia. Because the guide wire 101 entering the lung needs to be guided and monitored, the developing identifier therefore is arranged on the guide wire guide head 102. The developing identifier can display the implant through a fluoroscopy system, an ultrasonic imaging system, an MRI system, a computed X-ray tomography (CT) system or other remote imaging systems, among other similar systems. The guide wire 101 is displayed and guided through these systems, and in the embodiment, the spring formed by winding tungsten, tantalum and other metal wires with the diameters of 0.01 to 0.3 mm and having strong X-ray developing characteristic serves as the developing identifier. In the embodiment, the developing identifier and the guide wire guide head 102 are integrated into one part to achieve two functions. Except such mode, a developing identifier can be further arranged on the guide wire guide head 102. Certainly, when the implant surface of the present invention is not coated with the elastic membrane and is made from a material capable of performing development itself, such as, nickel-titanium alloy, the developing identifier may be not included.

For facilitating delivery of the guide wire 101, a guide wire handle 105 is arranged at the proximal end of the guide wire 101 and used for forward delivery of the guide wire 101, or for withdrawing the guide wire 101 after the implant 2 is delivered to the desired location.

Specifically, the push mechanism 110 comprises a hollow push steel cable 103 and a control handle 106 connected with the push steel cable 103, the guide wire 101 is sleeved with the push steel cable 103 and the implant 2, and the distal end of the push steel cable 103 is connected with a connecting piece 210 arranged at the proximal end of the implant 2. The adopted connecting mode is a detachable connection achieved through the connecting piece 210 arranged on the implant 2 and a connecting fitting piece 109 arranged at the distal end of the push steel cable 103. The connecting piece 210 and the connecting fitting piece 109 can adopt a variety of structures and connecting modes, for example, threaded connection. The connecting piece 210 with inner threads can be welded at the proximal implant end 201 of the implant 2, or inner threads can be directly lathed onto the proximal implant end 201 to serve as the connecting piece 210. The connecting fitting piece 109 with outer threads arranged at the distal end of the push steel cable 103, the inner thread of the connecting piece 210 can be in threaded connection with the outer thread of the push mechanism 110 during assembly, and then the implant 2 can be reliably fixed to the distal end of the push steel cable 103. After the implant 2 is pushed to reach a desired position, the connecting piece 210 of the implant 2 can be screwed out to be separated from the connecting fitting piece 109 of the push steel cable 103 by twisting the control handle 106 of the push steel cable 103. The connecting piece 210 and the connecting fitting piece 109 can also be made from other detachable parts, such as magnetic connecting devices, elastic fasteners and lassos, which are respectively arranged at the proximal implant end 201 of the implant 2 and the push steel cable 103 to achieve the detachable connection. As shown in FIG. 16, the connecting piece 210 arranged at the proximal implant end 201 is of a spiral connecting hook, similarly, a spiral connecting hook is also arranged at the distal end of the push steel cable 103, so they can be mutually and rotatably hooked together so that the implant 2 can be detachably and fixedly connected at the distal end of the push mechanism 110. After the implant 2 is pushed in place, the control handle 106 of the push steel cable 103 is turned in reverse to separate the two spiral connecting hooks.

During production and assembly, the assembly of the implant 2 and the guide wire 101 can be completed by means of a loader. First, the implant 2 penetrates into the loader, the implant 2 curled in a natural state can be constrained into a tube in a straight strip shaped delivery state by utilizing the space limitation of the loader. The guide wire 101 is assembled by inserting the push mechanism 110 into the proximal implant end 201 of the implant 2 and penetrating out of the distal implant end 202 of the implant 2 until a guide wire guide head 102 of the guide wire 101 penetrates out of the distal implant end 202 of the implant 2. Or in the circumstance that the distal implant end 202 is closed by an implant guide head 211, the guide wire 101 is inserted into the proximal implant end 201 of the implant 2 and mounted at the distal implant end 202 of the implant 2. The loader can be dismounted when the implant 2 is loaded to be in a straight delivery state under the constraint of the guide wire 101, and the connecting fitting piece 109 at the distal end of the push steel cable 103 in the push mechanism 110 is connected with the connecting piece 210 of the implant 2.

Figure 18:
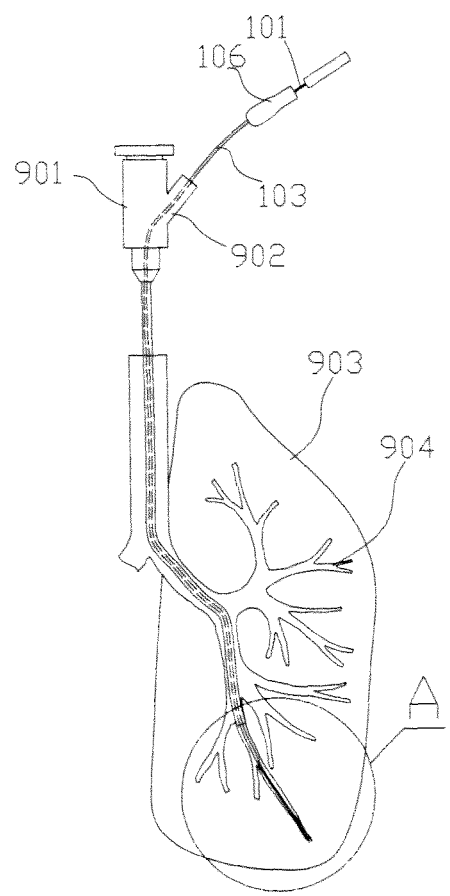
FIG. 18 is a schematic diagram showing the establishment of a working channel by a lung volume-reducing instrument provided in an embodiment of the present invention.
Figure 19:
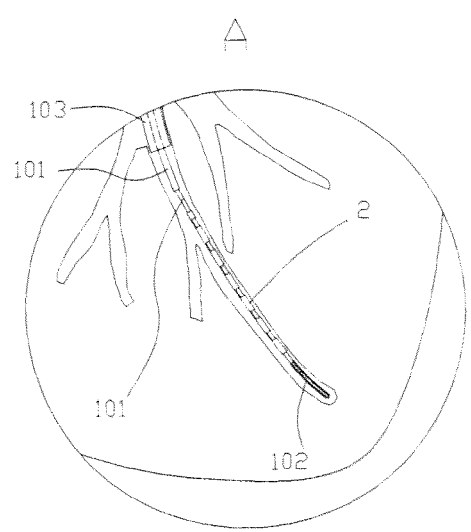
FIG. 19 is an enlarged view of the area A of FIG. 18.
Figure 20:
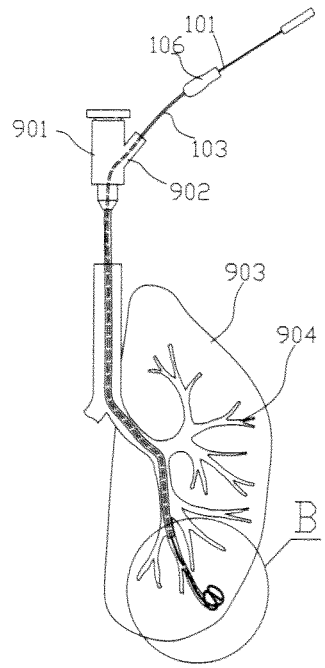
FIG. 20 is a schematic diagram showing the implantation of an implant provided in an embodiment of the present invention.
Figure 21:
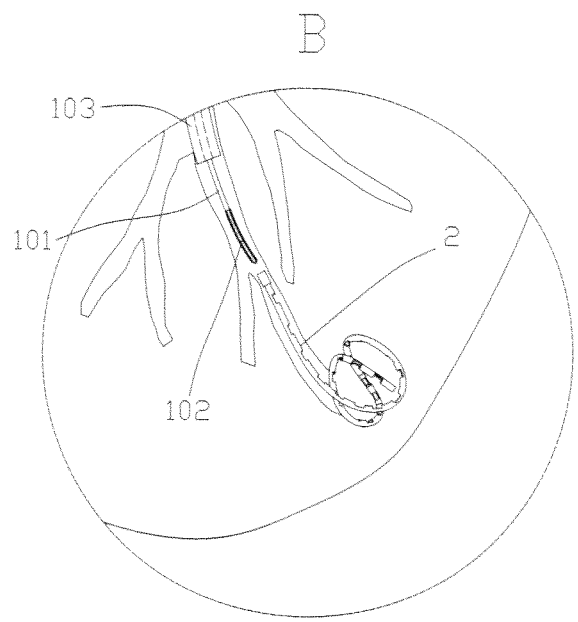
FIG. 21 is an enlarged view of the area B of FIG. 20.

As shown in FIGS. 18 to 21, the guide wire 101 which penetrates into the implant 2 in a sleeved mode is introduced into the bronchia 904 of the lung 903 through an operating channel 902 of a bronchoscope 901. After the channel is established through the guide wire 101 under the assistance of X rays, the implant 2 is pushed to the guide wire guide head 102 by utilizing the push steel cable 103 along the guide wire 101. Next, the guide wire 101 is withdrawn, and the implant 2 automatically restores its shape from the straight strip shaped delivery state formed due to the constraint of the guide wire 101 as shown in FIGS. 18 and 19 to its natural shape as shown in FIGS. 20 and 21 while the guide wire 101 is withdrawn. The emphysema area can be extruded and pulled in the restoration process, while the surrounding relatively-healthy lung tissues can also perform their physiological breathing functions, thereby achieving the lung volume-reducing effect. Then, the threaded connection between the connecting fitting piece at the distal end of the push steel cable 103 and the connecting piece 210 of the implant 2 can be loosened by turning the control handle 106 of the push steel cable 103, and the implant 2 is released.

The invention claimed is:

1. An assembly comprising:
  a lung volume-reducing elastic implant, characterized in that the implant is tubular and comprises a lumen, a proximal end, an elastic deformation part and a distal end, the elastic deformation part is located between the proximal end and the distal end and has a tube cavity, the elastic deformation part having a shape memory characteristic, the lung volume-reducing elastic implant is opened at least at the proximal end, the elastic deformation part is provided with a plurality of grooves at intervals along the longitudinal direction thereof, and each groove communicates with the tube cavity of the elastic deformation part; and
  a delivery device comprising a guidewire and a hollow push piece that has a distal end and a lumen, wherein the proximal end of the implant is detachably connected to the distal end of the hollow push piece, and the guidewire movably extends through the entire lumens of the implant and the hollow push piece.

2. The assembly according to claim 1, characterized in that angles α formed by cut directions of the grooves and the longitudinal direction of the elastic deformation part are 10-90° on the axially split spreading plane of the implant.

3. The assembly according to claim 2, characterized in that the implant further comprises an elastic membrane which at least coats the outer wall of the elastic deformation part.

4. The assembly according to claim 3, characterized in that the grooves are filled with the elastic membrane.

5. The assembly according to claim 1, characterized in that the implant has an outer diameter that is gradually increased from the distal end to the proximal end.

6. The assembly according to claim 1, characterized in that the distal end of the implant is extended outwardly to be connected with a flexible guide head, the guide head is coaxial with the distal end of the implant and closes the distal end of the implant, and the guide head is provided with a developing identifier.

7. The assembly according to claim 1, characterized in that a detachable connecting piece is arranged at the proximal end of the implant.

8. An assembly comprising:
  a lung volume-reducing elastic implant, characterized in that the implant is tubular and comprises a lumen, a proximal end, an elastic deformation part and a distal end, the elastic deformation part is located between the proximal end and the distal end and has a tube cavity, the elastic deformation part having a shape memory characteristic, the lung volume-reducing elastic implant is opened at least at the proximal end, the elastic deformation part is provided with a plurality of grooves at intervals along the longitudinal direction thereof, and each groove communicates with the tube cavity of the elastic deformation part; and
  a delivery device comprising a guidewire and a hollow push piece that has a distal end and a lumen, wherein the proximal end of the implant is detachably connected to the distal end of the hollow push piece, and the guidewire movably extends through the lumens of the implant and the push piece; and
  wherein the distal end of the guidewire is provided with a soft guidewire guide head coaxial with the guidewire, and the guidewire guide head has an outer diameter consistent with that of the guidewire.

9. The assembly of claim 8, characterized in that the guidewire guide head comprises a guide post, and a spring fixed and sleeved outside of the guide post, and the guide post and the guidewire are integrally structured or the guide post is fixedly connected to the distal end of the guidewire, and wherein the spring has a developing identifier.

10. The assembly according to claim 1, characterized in that angles α formed by cut directions of the grooves and the longitudinal direction of the elastic deformation part are 10-90° on the axially split spreading plane of the implant.

11. The assembly according to claim 10, characterized in that the implant further comprises an elastic membrane which at least coats the outer wall of the elastic deformation part.

12. The assembly according to claim 11, characterized in that the grooves are filled with the elastic membrane.

13. The assembly according to claim 8, characterized in that the implant has an outer diameter that is gradually increased from the distal end to the proximal end.

14. The assembly according to claim 8, characterized in that the distal end of the implant is extended outwardly to be connected with the guidewire guide head, the guide head being coaxial with the distal end of the implant and closes the distal end of the implant, and the guidewire guide head is provided with a developing identifier.

15. The assembly according to claim 8, characterized in that a detachable connecting piece is arranged at the proximal end of the implant.

* * * * *